United States Patent
Kanda et al.

(10) Patent No.: US 9,018,627 B2
(45) Date of Patent: Apr. 28, 2015

(54) INSPECTION APPARATUS

(71) Applicant: Hitachi High-Technologies Corporation, Minato-ku, Tokyo (JP)

(72) Inventors: Nobuhiro Kanda, Izumo (JP); Hiroshi Mukai, Ishioka (JP); Masatoshi Watanabe, Ushiku (JP); Kazuyuki Sugimura, Hitachinaka (JP); Katsuyasu Inagaki, Hitachinaka (JP); Yuichirou Iijima, Yorii (JP)

(73) Assignee: Hitachi High-Technologies Corporation, Tokyo (JP)

( * ) Notice: Subject to any disclaimer, the term of this patent is extended or adjusted under 35 U.S.C. 154(b) by 197 days.

(21) Appl. No.: 13/788,544

(22) Filed: Mar. 7, 2013

(65) Prior Publication Data

US 2013/0301041 A1 Nov. 14, 2013

(30) Foreign Application Priority Data

May 11, 2012 (JP) ................................. 2012-109055

(51) Int. Cl.
| | | |
|---|---|---|
| G01N 21/95 | (2006.01) | |
| G01N 21/94 | (2006.01) | |
| H01L 21/66 | (2006.01) | |
| H01L 21/67 | (2006.01) | |

(52) U.S. Cl.
CPC ............ *G01N 21/9505* (2013.01); *G01N 21/94* (2013.01); *G01N 21/9501* (2013.01); *H01L 22/12* (2013.01); *H01L 21/67028* (2013.01); *H01L 21/67288* (2013.01)

(58) Field of Classification Search
CPC ................................................. G01N 21/9501
See application file for complete search history.

(56) References Cited

U.S. PATENT DOCUMENTS

| | | | | |
|---|---|---|---|---|
| 5,916,366 A | * | 6/1999 | Ueyama et al. | ................... 118/52 |
| 6,005,660 A | | 12/1999 | Yoshida et al. | |
| 6,832,616 B2 | * | 12/2004 | Miyazaki | ...................... 134/98.1 |
| 7,372,559 B2 | | 5/2008 | Haller et al. | |
| 7,420,668 B2 | | 9/2008 | Zama et al. | |
| 8,062,471 B2 | * | 11/2011 | Mikhaylichenko et al. | ......................... 156/345.37 |
| 2012/0144938 A1 | | 6/2012 | Inagaki et al. | |

FOREIGN PATENT DOCUMENTS

| | | |
|---|---|---|
| JP | 7-230037 A | 8/1995 |
| JP | 2000-230910 A | 8/2000 |
| JP | 2010-236948 A | 10/2010 |
| JP | 2011-75351 A | 4/2011 |

* cited by examiner

*Primary Examiner* — Evan Pert
(74) *Attorney, Agent, or Firm* — Crowell & Moring LLP (57) ABSTRACT

In semiconductor surface inspection apparatus, foreign matter that sticks to the wafer can reduce the quality of the wafer. The present invention is directed to improving the internal cleanliness of the apparatus. Specifically, during rotation of a semiconductor wafer, foreign matter suspended in an atmosphere surrounding the wafer is attracted to a central section of the wafer, and that while heading from the central section of the wafer, towards an outer edge thereof, the foreign matter is most likely to stick to the wafer. In conventional techniques, sufficient consideration is not given to such likelihood of foreign matter sticking. This invention supplies a medium from two directions to an inner circumferential section of a substrate. In accordance with the invention, foreign matter that sticks to a wafer can be reduced more significantly than in the conventional techniques.

21 Claims, 13 Drawing Sheets

INSPECTION APPARATUS

BACKGROUND OF THE INVENTION

1. Field of the Invention

The present invention relates to a surface inspection apparatus that inspects foreign substances, flaws, and other defects present on surfaces of objects such as semiconductor wafers or ceramic substrates.

2. Description of the Related Art

If foreign substances, flaws, or other defects are present on the surface of a semiconductor wafer, semiconductor devices fabricated using such semiconductor wafer will be defective. Accordingly, the wafer needs inspection by a surface inspection apparatus to scan for defects. The surface inspection apparatus irradiates the wafer surface with laser light, receives the light reflected from the wafer, and compares the light signal with a threshold value to determine whether the wafer is nondefective. At this time, the wafer is fixed by a substrate-holding jig and rotated at a predetermined speed by a spindle. Simultaneously with the rotation by the spindle, the wafer is moved rectilinearly by a stage. The rotation by the spindle and the linear movement by the stage make the laser light helically scan the wafer surface in relative form. The entire wafer surface is inspected during the scan. In manufacturing lines, the inspection apparatus may also be used with a view to monitoring an occurrence status of dust raised from manufacturing apparatuses.

With the miniaturization of semiconductor circuit width in recent years, the foreign substances, flaws, and other surface defects becoming a problem if they stick to wafers are also being miniaturized in size. The dimensional miniaturization of these defects is, in turn, increasing the number of defects likely to become a problem, and this tendency is bringing about a call for further improvement of the internal cleanliness of apparatuses.

Among existing techniques relating to the cleaning of an inspection apparatus are those described primarily in JP-2011-75351-A, JP-2010-236948-A, and JP-1995-230037-A. JP-2011-75351-A discloses a technique in which multiple fan-filtering units, each of which comprises a fan and exhaust unit for supplying clean air, are disposed and flow rates of air in each of the fans and exhaust units are controlled to suppress a disturbance in the apparatus internal air flow and reduce the volume of foreign matter likely to stick to a wafer.

JP-2010-236948-A discloses suppressing a disturbance in an air flow near a semiconductor wafer by incorporating louver and exhaust unit structural design considerations for reduced sticking of foreign matter to the wafer.

JP-1995-230037-A discloses adopting a downward flow scheme and exhaust unit structure for reduced sticking of foreign matter to a wafer.

Other related techniques include those proposed in JP-2000-230910-A, U.S. Pat. No. 7,420,668, U.S. Pat. No. 7,372,559, and U.S. Pat. No. 6,005,660.

SUMMARY OF THE INVENTION

The present invention is based upon the inventors' findings that during rotation of a semiconductor wafer, foreign matter suspended in an atmosphere surrounding the wafer is attracted to a central section of the wafer, and that while heading from the central section of the wafer, towards an outer edge thereof, the foreign matter is most likely to stick to the wafer.

More specifically, this event is accounted for as follows. (1) While the semiconductor wafer is rotating at several thousands of revolutions per minute (rpm), inspection is conducted and friction between the wafer and the air resulting from the rotation generates an airflow similar to that formed by a disc fan. (2) The airflow near the rotating wafer increases in circumferential flow velocity as it moves closer to the outer edge of the wafer. Thus, the airflow gains a speed by an action of centrifugal force to move to radial outside of the wafer and move further outward from the wafer surface. Compared with a circumferential section of the wafer, therefore, the central section thereof assumes a negative pressure and moves the airflow to the central section of the wafer. (3) The airflow that has moved to the central section of the wafer moves away therefrom, towards the outer edge and then moves to the outside of the wafer. (4) For this reason, the foreign matter that sticks to the rotating wafer is considered to stick while traveling along a route similar to that of the airflow.

The rotational airflow generated by the rotation of the wafer spinning at several thousands of rpm has a higher flow velocity than an airflow supplied from the fan-filtering unit disclosed in Patent Document 1, and tends to become a ruling flow inside the inspection unit. A risk of the atmosphere being stirred up or disturbed by the rotational airflow, therefore, cannot be completely eliminated by merely adopting the method disclosed in JP-2011-75351-A.

JP-1995-230037-A discloses the downward flow scheme in which clean air is supplied downward from a direction above the wafer. However, parts of an optical system which serves as a core of inspection are usually arranged above the wafer and no consideration is given to in what form the system for supplying the airflow is to be disposed. Even after the layout of the optical system parts has been changed to enable the application of the downward flow scheme, if parts exist above the wafer, a disturbance in the airflow at rear of the parts may cause foreign matter to stem from the parts. If this actually happens, the foreign matter is most likely to stick to the wafer.

The present invention is intended to reduce the volume of foreign matter likely to stick to a wafer.

The present invention features supplying a medium to an inner circumferential section of a substrate from two directions.

In accordance with the present invention, the volume of foreign matter likely to stick to the wafer can be reduced as compared with conventional techniques.

DESCRIPTION OF THE PREFERRED EMBODIMENTS

Hereunder, embodiments of the present invention will be described using the accompanying drawings.

First Embodiment

Figure 1:
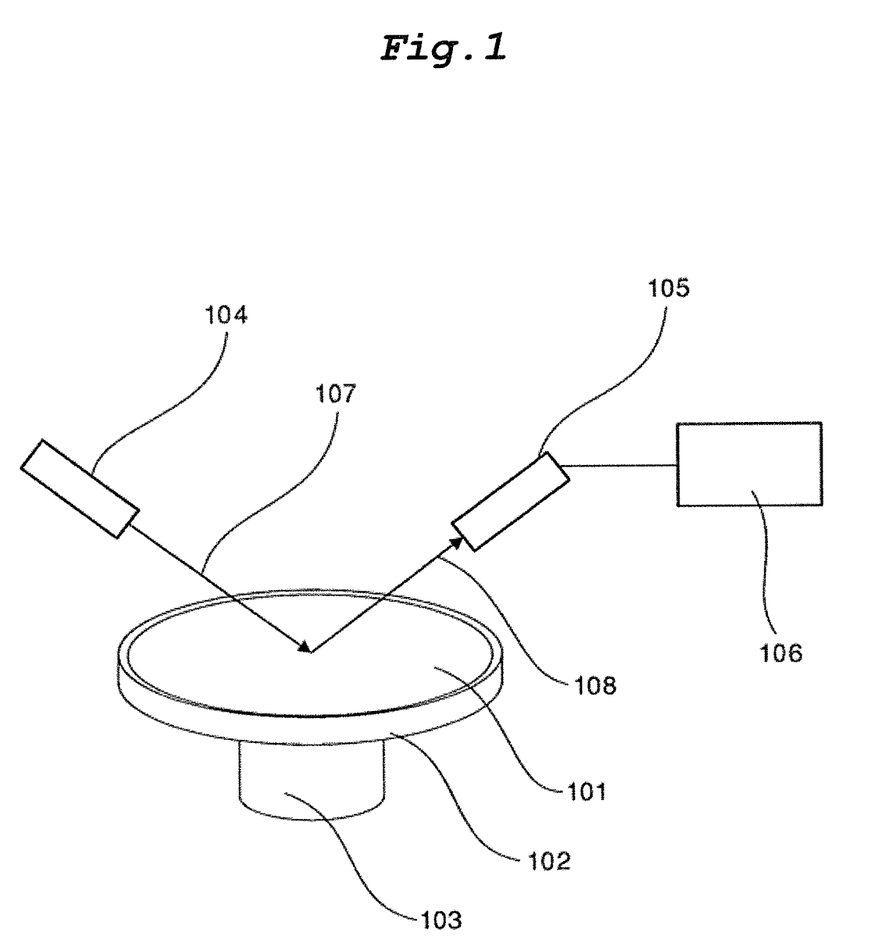
FIG. 1 is a schematic diagram of an inspection apparatus according to a first embodiment.

A schematic diagram of an inspection apparatus according to a first embodiment is shown in FIG. 1. A laser light emitter 104 emits laser light 107 towards a substrate 101. After the emission of the laser light 107, backscattered light 108 from the substrate 101 is received by an optical system 105 for detection. The detected signal is compared with a threshold level by a processing unit 106, and if the detected signal level is higher than the threshold level, the signal is determined to indicate presence of foreign matter or a surface defect such as a flaw. If the signal level is lower than the threshold level, on the other hand, the signal is determined to be a false report. In the detection step, the substrate 101 is fixed by a substrate-holding jig 102 and rotated by a spindle 103. During substrate rotation, an illumination region that the laser light emitter 104 has formed upon the substrate 101 is scanned in a circumferential direction. Various control described later herein is conducted by the processing unit 106.

Figure 2:
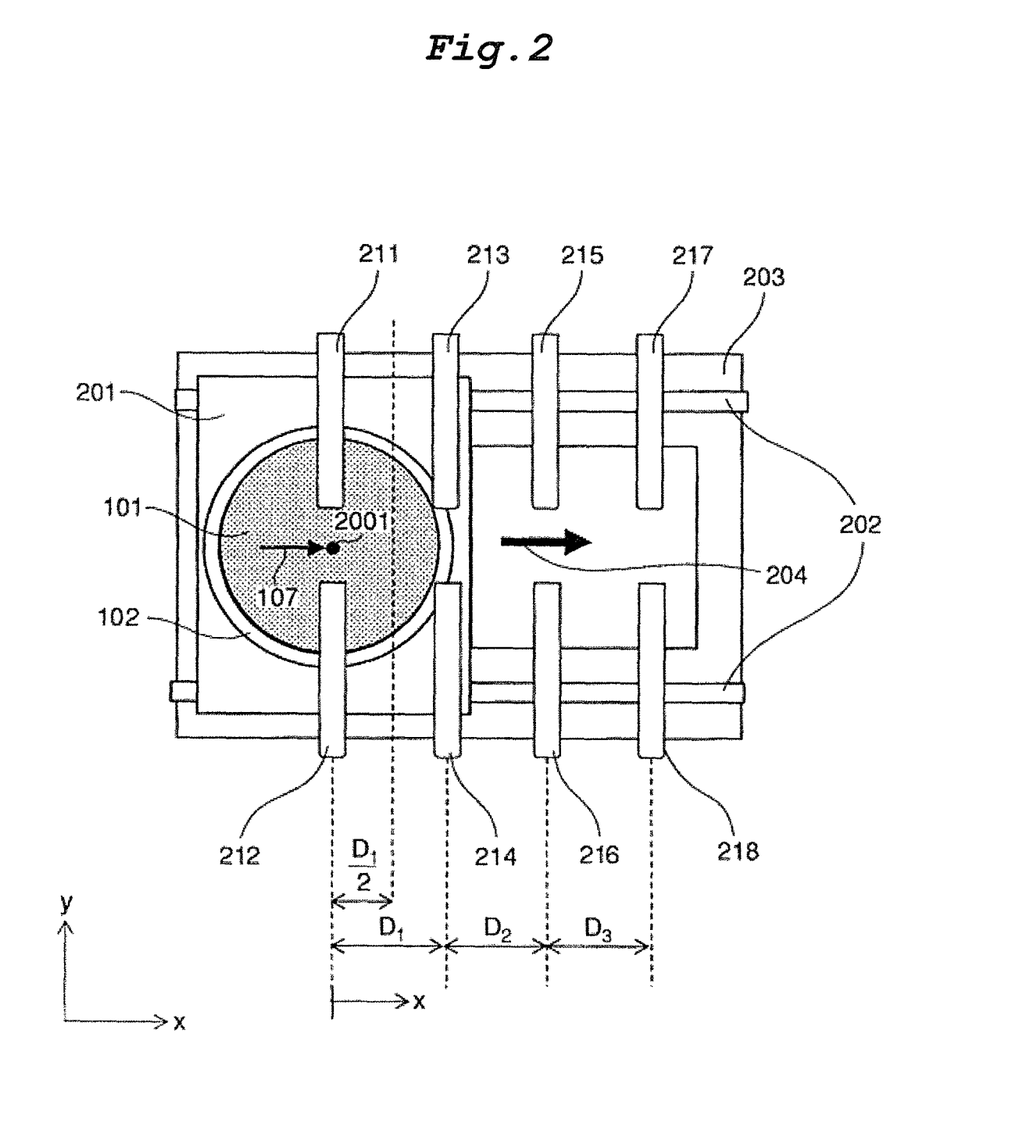
FIG. 2 is a top view showing a schematic configuration of the inspection apparatus according to the first embodiment.

FIG. 2 is a top view of the inspection apparatus existing when viewed from a direction above the substrate 101 in the present embodiment. The substrate 101 is retained by the substrate-holding jig 102. The substrate-holding jig 102 is mounted on the spindle 103. The spindle 103 is mounted on a moving stage 201. The moving stage 201 moves the substrate 101 rectilinearly in a direction of arrow 204, along a surface of a stage 202 disposed on a stage 203. Since the substrate 101 is rotated by the spindle 103 and moved by the moving stage, the laser light 107 causes the illumination region 2001 on the substrate 101 to draw a helical path in relative form with respect to the substrate 101.

In a moving zone of the moving stage 201, ducts 211 to 218 for supplying an airflow, one example of a medium, are arranged in a moving direction of the stage 201. The medium may be a nitrogen gas, an argon gas, or any other appropriate inert gas, instead of air. A distance between the ducts 212 and 214 is expressed in terms of $D_1$ (this also applies to a distance between the ducts 211 and 213), a distance between the ducts 214 and 216 is expressed in terms of $D_2$ (this also applies to a distance between the ducts 213 and 215), and a distance between the ducts 216 and 218 is expressed in terms of $D_3$ (this also applies to a distance between the ducts 215 and 217), where $D_1 = D_2 = D_3$.

Figure 3A:
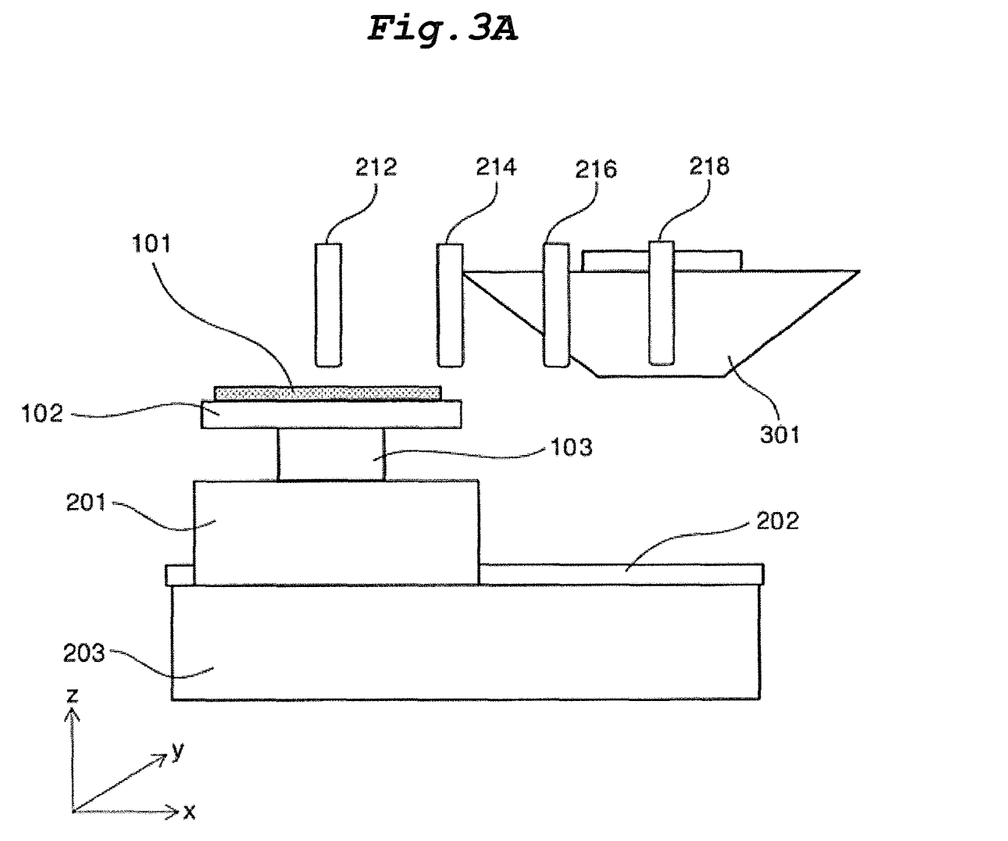
FIGS. 3A and 3B are front views showing the schematic configuration of the inspection apparatus according to the first embodiment.
Figure 3B:
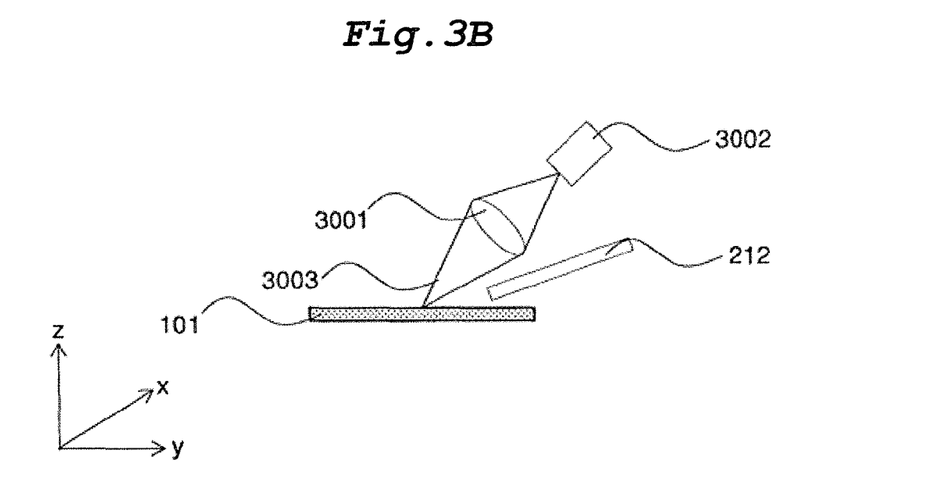

FIGS. 3A and 3B are diagrams representing a relationship between an optical system 301 and the ducts 211 to 218. FIG. 3A shows the inspection apparatus existing when viewed from an x direction in the present embodiment. The optical system 301 includes an illumination optical system such as the laser light emitter 104, and the detection optical system 105. The optical system 301 is disposed above the substrate 101, and the ducts 211 to 218 are disposed around the optical system 301.

FIG. 3B shows the inspection apparatus existing when viewed from a y direction in the present embodiment. The detection optical system 105 includes a lens 3001 that converges the light backscattered from the substrate 101, and a photoelectric conversion element 3002 that conducts a photoelectric conversion of the converged light. The lens 3001 is provided to acquire the light from the substrate 101 in a certain zone 3003, and the duct 212, for example, is disposed outside the zone 3003 so as not to trouble or inconvenience the detection of the light from the substrate 101 (the same also applies to the other ducts). The detection optical system in the present embodiment may include a plurality of combinations of the lens 3001 and photoelectric conversion element 3002 shown in FIG. 3B.

Figure 4:
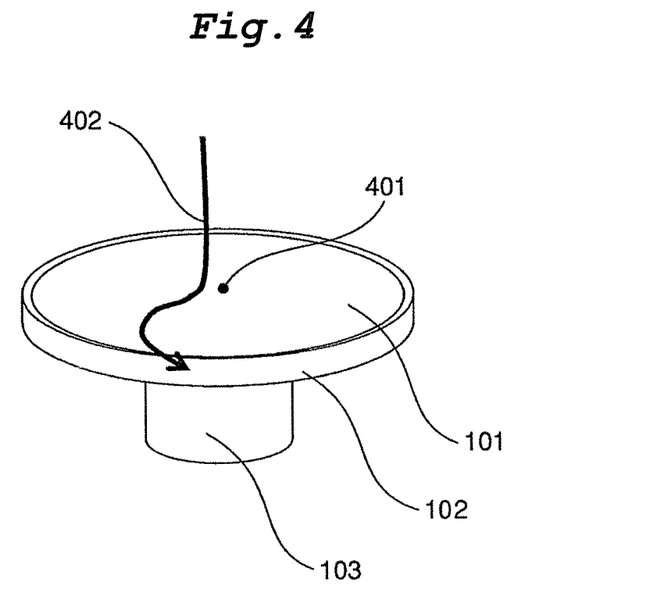
FIG. 4 is a schematic diagram of an airflow formed around a substrate when no duct is used.

Next, layers of clean air that the ducts 211 to 218 form on the substrate 101 in the present embodiment are described below. An example of not using the ducts 211 to 218 is first described below. FIG. 4 is a diagram illustrating an airflow formed around the substrate 101 when the ducts 211 to 218 are not used. The substrate 101 is supported by the substrate-holding jig 102, and when viewed from above, the substrate is rotated counterclockwise by the spindle 103. The rotation of the substrate 101 generates an airflow 402 heading downward from the direction above the substrate 101, towards a central section of the substrate, and then near the surface of the substrate 101, the airflow 402 next heads from the central section of the substrate, towards an outer edge thereof. Additionally, as the airflow 402 approaches the outer edge of the substrate 101, it decreases in circumferential velocity and increases in disturbance. Much of the foreign matter considered to exist in the airflow 402 moves along substantially the same route as that of the airflow, and sticks to the substrate 101 in a course of the movement.

Figure 5:
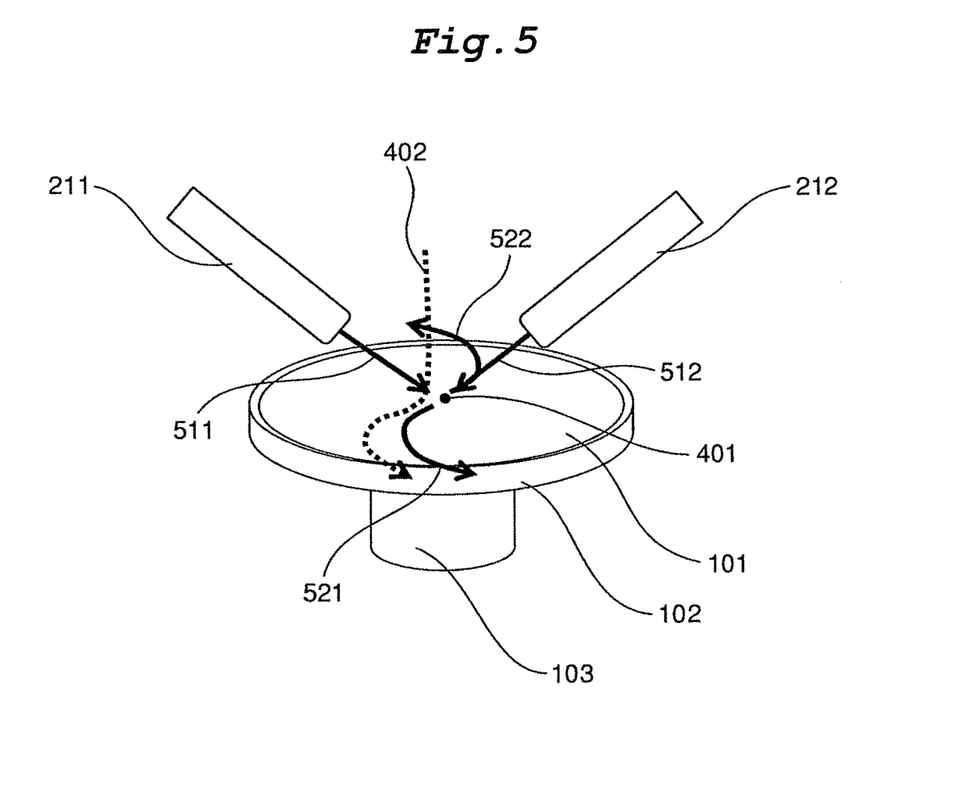
FIG. 5 is a schematic diagram of an airflow formed around the substrate when duct is used.

An example of using the ducts 211 to 218 is next described below. FIG. 5 is a diagram illustrating an airflow formed around the substrate 101 when the ducts 211 to 218 are used. The ducts 211 and 212, especially, lines of projection onto the substrate 101, are arranged in mutually opposed form to face an inner circumference, more specifically the central section 401, of the substrate 101, and supply airflows 511 and 512, respectively, that are cleaner than an atmosphere surrounding the substrate 101, towards the central section of the substrate 101. The clean airflows 511, 512 are created as a result of cleaning with a filter or the like inside the ducts 211, 212.

During the rotation of the substrate 101, the clean airflows 511 and 512 become clean airflows 521 and 522 each heading from the central section 401 of the substrate 101, towards the outer edge thereof. The clean airflows 521, 522 stream near the entire surface of the substrate 101. That is to say, highly clean layers of air are formed on or directly near the substrate 101. The airflow 402 lower than the airflows 521, 522 in cleanliness streams externally to the airflows 511, 512, 521, 522, thus allowing the volume of foreign matter likely to stick to the substrate 101.

Figure 12:
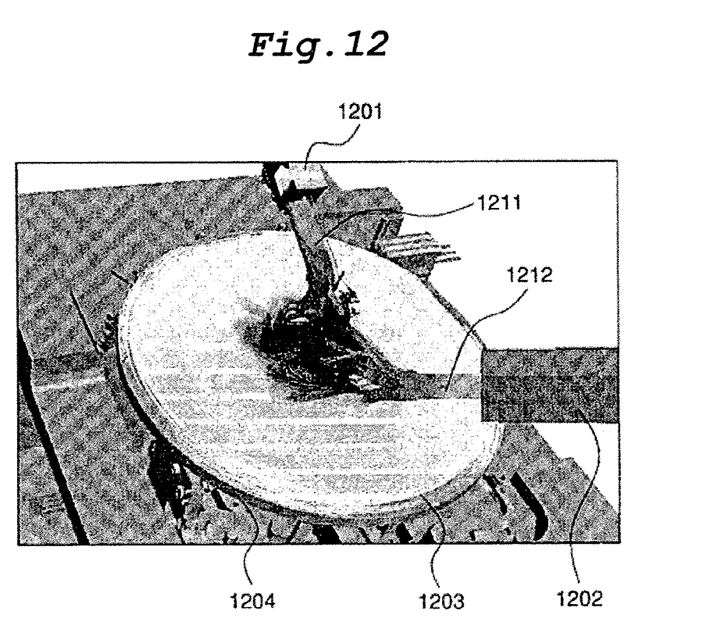
FIG. 12 is a diagram illustrating an example of supplying an airflow at an average flow velocity of 5 m/s from two ducts, 1201 and 1202, to a substrate 1203.
Figure 13:
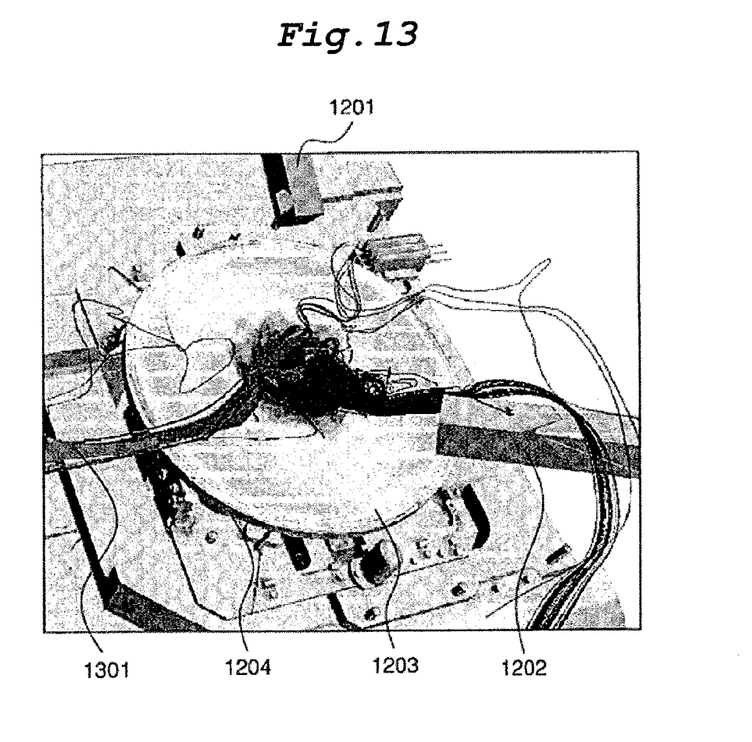
FIG. 13 is a diagram illustrating an example of supplying an airflow at an average flow velocity of 1 m/s from the two ducts, 1201 and 1202, to the substrate 1203.

When the clean airflows 511, 512 are supplied, their flow velocities can also be controlled. This characteristic is described below using FIGS. 12 and 13. FIG. 12 is a diagram illustrating an example of supplying an airflow at an average flow velocity of 5 m/s from two ducts, 1201 and 1202, to a substrate 1203 mounted on a substrate-holding jig 1202. FIG. 13 is a diagram illustrating an example of supplying an airflow at an average flow velocity of 1 m/s from the two ducts, 1201 and 1202, to the substrate 1203 mounted on the substrate-holding jig 1204. FIG. 12, which shows airflows supplied at higher flow velocities than the airflow shown in FIG. 13, indicates that flow lines 1211 and 1212 that pass through a neighborhood of the substrate 1203 move from the ducts 1201 and 1202, respectively, onto the substrate 1203. Meanwhile, FIG. 13, which shows the airflow of a lower flow velocity, indicates that a flow line 1301 moves from a non-duct region, onto the substrate 1203. These facts indicate that if the flow velocities of cleaner airflows are appropriately controlled to a fixed level as in FIG. 12, the cleaner airflows can be supplied to the central section of the substrate 1203 for improved cleanliness in the neighborhood of the wafer.

Referring back to FIG. 5, when air is supplied from the ducts 211, 212 at a fixed flow velocity or more, the clean airflow 511 and the clean airflow 512 collide against each other and also against the substrate 101, thus causing a pressure of the air near the central section of the substrate 101 to rise relative to a pressure of its surrounding region. This prevents entry of the low-cleanliness airflow 402 more reliably and maintains the neighborhood of the substrate surface at a high level of cleanliness.

Additionally, if the airflows 511, 512 supplied from the ducts 211, 212 are controlled to increase in both flow velocity and flow rate, this increases thickness of the clean layers of airflow that the airflows 511, 512 form on the substrate 101, thus further reduces the volume of foreign matter stirred up from the outside of the clean layers of airflow by a disturbance in the airflows at the outer edge, and results in a further reduced volume of foreign matter sticking to the wafer. Furthermore, the increase in the flow rates of the airflows 511, 512 increases the flow velocities at which the airflows move in a radially outward direction of the substrate 101, at the outer edge thereof. The foreign matter that has been stirred up by the disturbance is therefore discharged from the surface of the substrate 101 more rapidly, with the result that the volume of foreign matter likely to stick is also further reduced.

Since the clean airflows 511, 512 need only to be supplied towards the central section of the substrate 101, it is unnecessary for the ducts 211, 212 to completely face each other. If both face each other, however, the central section of the substrate 101 can be boosted in pressure effectively and for the reason described above, such orientations of the ducts 211, 212 are more effective for reducing the amount of contamination with foreign matter.

The opposed layout of the ducts 211, 212 further yields the following advantageous effect. That is, during slow spindle rotation at several tens of rpms or several hundreds of rpm, the airflow by the rotation of the substrate 101 is not a ruling one. Instead, airflows from the ducts 211, 212 become ruling ones. As shown in FIG. 5, when the ducts 211, 212 are arranged to face each other for collisions between the airflows 511, 512, these clean airflows have a relatively uniform density on or directly near the surface of the substrate 101, compared with the airflow formed when the ducts are not in opposed arrangement. The result is that the amount of contamination with foreign matter can also be reduced during slow rotation.

Figure 6:
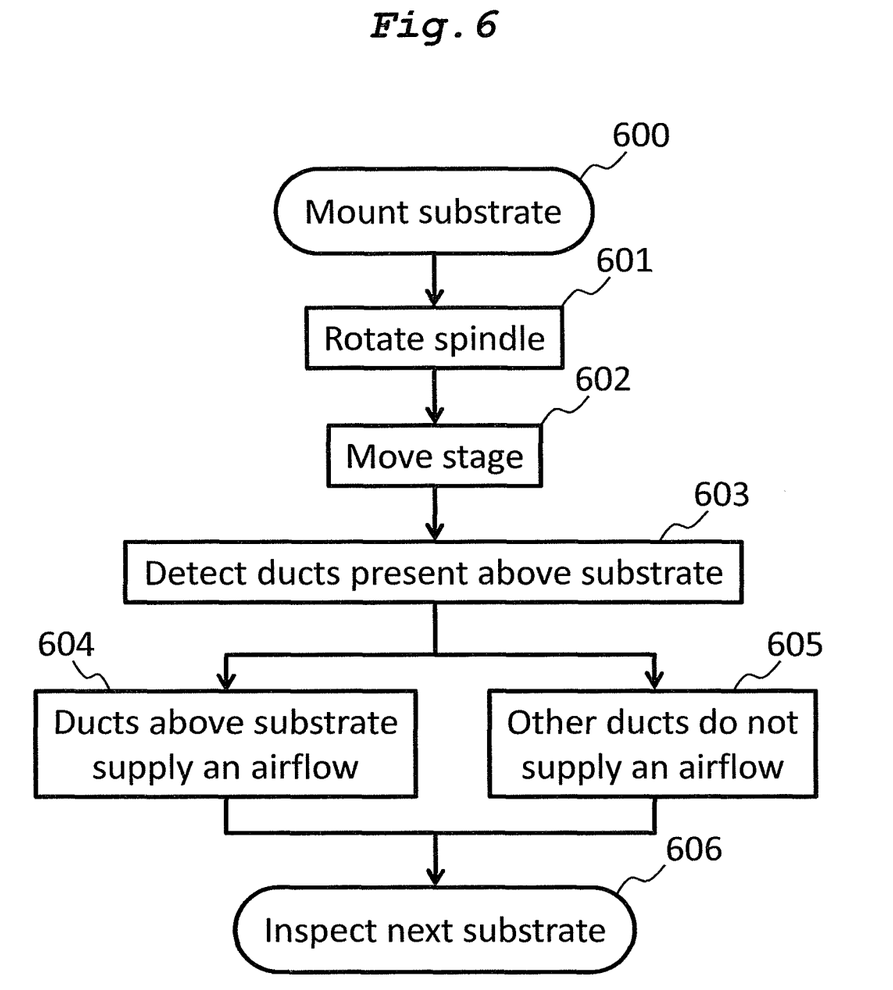
FIG. 6 is a flowchart that shows an operational sequence of the inspection apparatus according to the first embodiment.

Next, an operational sequence of the inspection apparatus according to the present embodiment is described below using a flowchart of FIG. 6. First, the substrate 101 is mounted on the substrate-holding jig 102 (step 600). The processing unit 106 activates the spindle 103 to rotate the substrate 101 (step 601). After confirming that the rotation of the substrate 101 has reached a fixed rotating speed for inspection, the processing unit 106 moves the moving stage 201 (step 602). The processing unit 106 next detects any ducts arranged near the surface of the substrate 101 (step 603). The ducts that have been determined to be present near the surface of the substrate 101 open respective internal valves to supply clean airflows (step 604). If no ducts are determined to be present near the surface of the substrate 101, the respective internal valves are closed so as not to supply a clean airflow (step 605). Inspection takes place between steps 601 and 604. After the inspection of the entire substrate surface, next substrate is inspected (step 606).

Step 603 is described in further detail below. Constantly changing central positions of the substrate 101 are defined in an internal program of the processing unit 106 beforehand from a horizontal moving speed and other factors of the substrate 101, and ducts present near the surface of the substrate 101 are detected from a relationship between the central position thereof at a specific time and previously saved positions of each duct.

To be more specific, if the horizontal moving speed of the moving stage 201 is expressed as "v", a distance through which the center of the substrate 101 moves while a time "t" elapses from a start of the horizontal movement can be expressed as "vt" in the x-axis direction represented in FIG. 2. If the distances between the ducts arranged in the moving direction of the substrate 101 are expressed here in terms of $D_1$ and $D_2$ as shown in FIG. 2, the ducts above the substrate 101 can be detected by setting the program as follows:

$$0 \leq vt < D_1/2 \rightarrow \text{Supply from ducts 211,212} \tag{1}$$

$$D_1/2 \leq vt < (D_1+D_2/2) \rightarrow \text{Supply from ducts 213,214} \tag{2}$$

$$(D_1+D_2/2) \leq vt < (D_1+D_2+D_3/2) \rightarrow \text{Supply from ducts 214,216} \tag{3}$$

$$(D_1+D_2+D_3/2) \leq vt \leq (D_1+D_2+D_3) \rightarrow \text{Supply from ducts 217,218} \tag{4}$$

Ideally, while the substrate 101 is moving horizontally, a clean airflow keeps the pressure near the center of the substrate 101 higher than its surroundings at all times. Supply of the clean airflow, however, is not limited to the above-described control method. During the inspection time (this time can also be expressed as a time during which the moving stage 201 is moving), a substantially clean layer of air needs only to be present on or directly near the surface of the substrate 101. In addition, while the number of opposed duct pairs in the present embodiment is four, the number of ducts is not limited to the embodiment and any other number suffices if a substantially clean layer of air is formed on or directly near the surface of the substrate 101.

In accordance with the present embodiment, the volume of foreign matter likely to stick to the substrate 101 can be reduced as compared with the conventional techniques discussed earlier herein.

Second Embodiment

The following describes a second embodiment. The second embodiment has the following two differences from the first embodiment: (1) ducts are arranged more densely than in the first embodiment, and (2) a temperature of airflows supplied from the ducts is changed (controlled).

Figure 7:
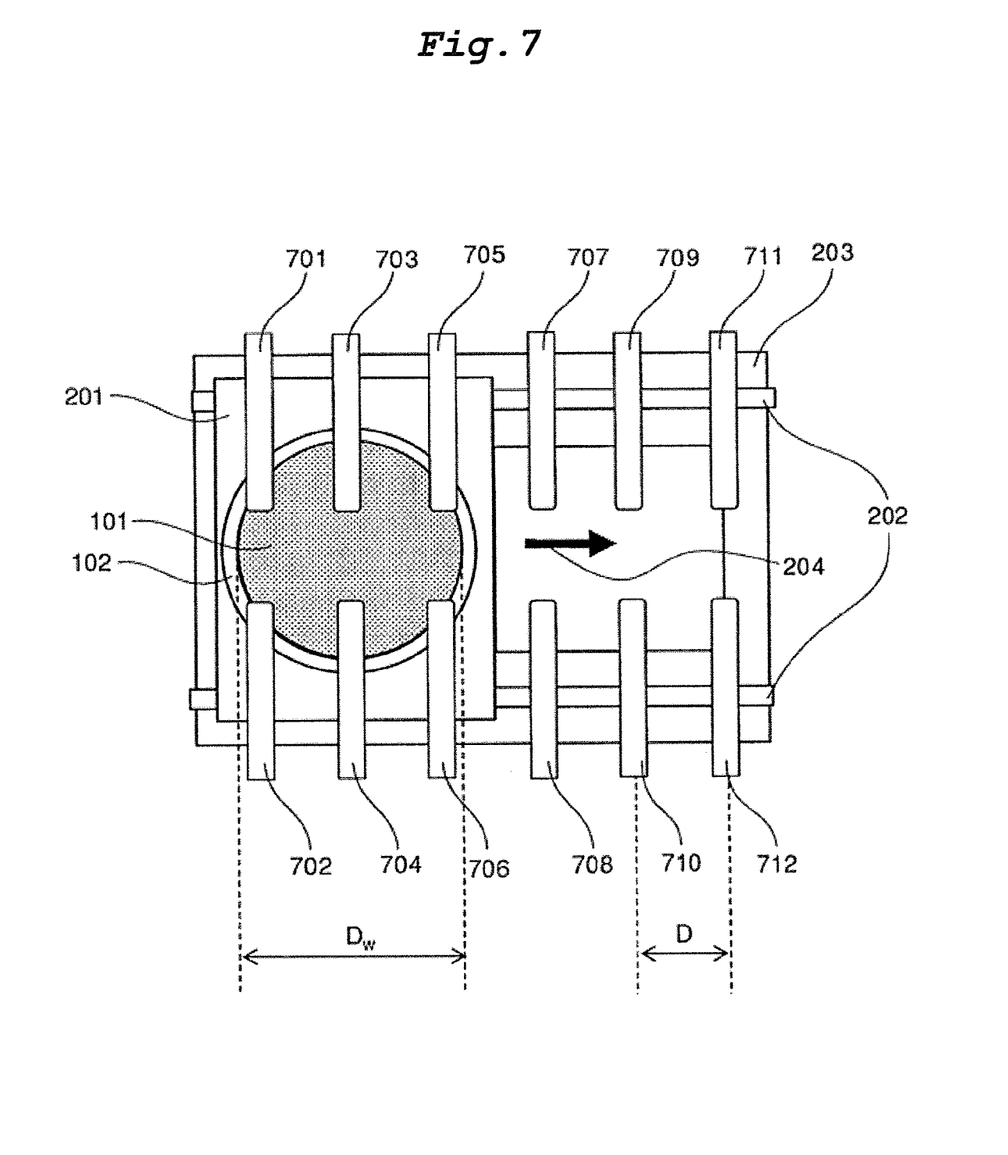
FIG. 7 is a top view showing a schematic configuration of an inspection apparatus according to a second embodiment.

FIG. 7 is a top view illustrating an inspection apparatus according to the present embodiment. In the present embodiment, the ducts 701 to 712 are arranged so that distance D between any two ducts, in a direction of arrow 204, is shorter than $D_w/2$, a radius of a substrate 101.

The airflows supplied in the present embodiment are described below using FIG. 8. In the present embodiment, the ducts 703, 704 are oriented towards a central section 401 of the substrate 101, and the ducts 701, 702, 706 are arranged externally to the ducts 703, 704 and oriented towards an outer edge of the substrate 101.

When viewed from above, the substrate 101 is rotating counterclockwise by an action of a spindle 103. In the present embodiment, a clean airflow is supplied only from the ducts 701, 703, 704, 706, and no clean airflow is supplied from the ducts 702, 705.

Clean hot airflows 801 and 802 that have been heated by a heater or the like to a temperature higher than an ambient temperature, and passed through the filter at least once, are supplied from the ducts 703, 704. The rotation of the substrate 101 causes the hot airflows 801, 802 to head from the central section of the substrate 101, towards the outer edge of the substrate, and become clean hot airflows 811, 812 that stream near the substrate surface.

On the other hand, clean cold airflows 821 and 822 that have been cooled by a cooler or the like to a temperature equal to or lower than the ambient temperature, and passed through the filter at least once, are supplied from the ducts 701, 706. The clean airflows 821, 822 stream above the clean hot airflows 811, 812. Forming these airflows causes the clean hot airflows to stream near the surface of the substrate 101, and forms a flow field in which the clean cold airflows stream externally to the clean hot airflows.

Operational actions of the present embodiment are accounted for as follows: if a temperature gradient exists around microscopic foreign matter as small as nearly submicrons (submicrometers) in diameter, heat migration exerts upon the foreign matter a force making it move to lower-temperature regions, such that the foreign matter moves to the lower-temperature regions. In FIG. 8, warmer airflows exist at sections closer to the substrate 101, cooler airflows exist at sections more distant from the substrate 101, and hence even when the foreign matter is present in the clean hot airflows 811, 812 or the clean cold airflows 821, 822, the foreign matter undergoes the force to move away from the substrate 101 and leave the neighborhood thereof, which in turn allows reduction in the amount of contamination with foreign matter.

Figure 9:
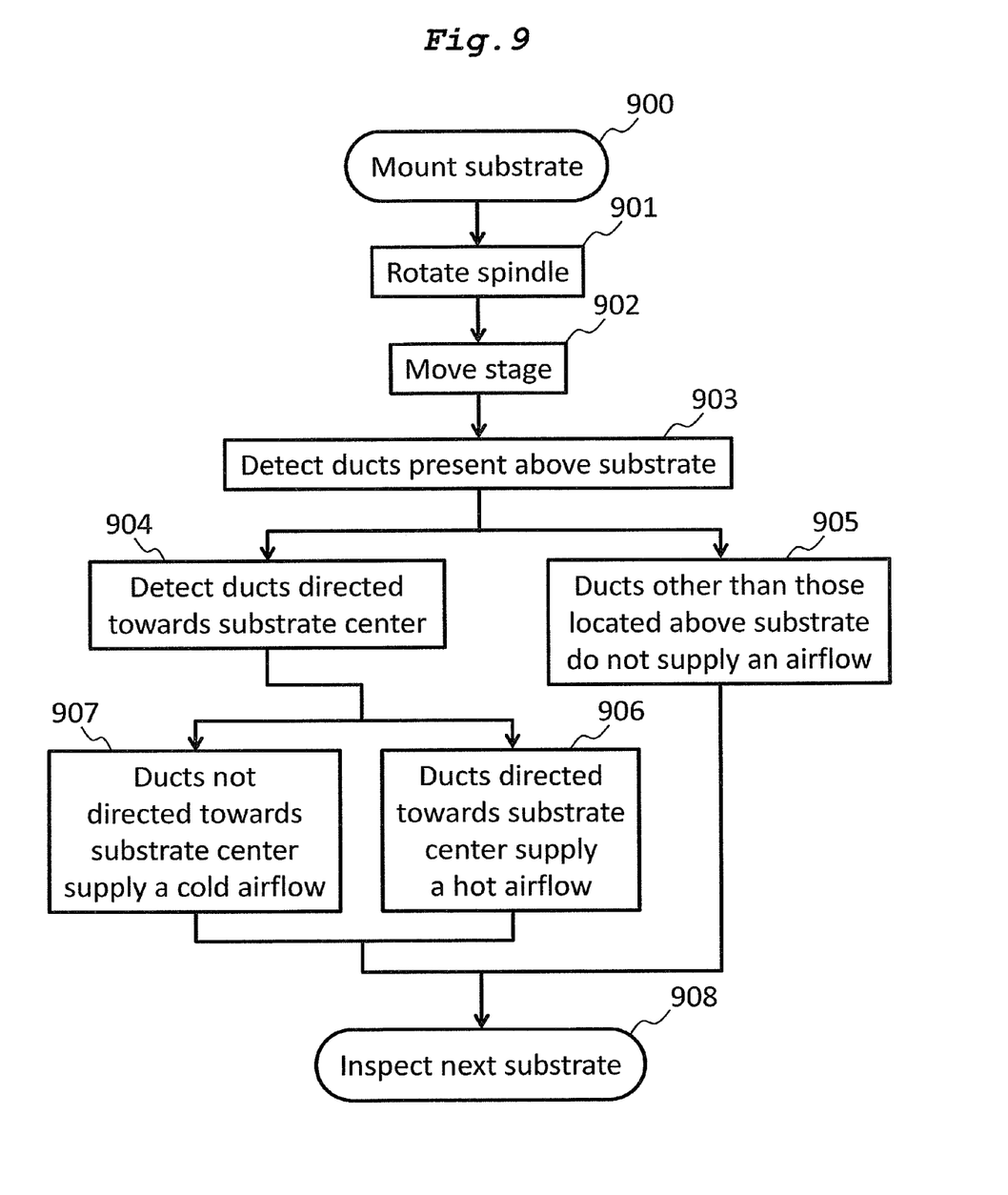
FIG. 9 is a flowchart that shows an operational sequence of the inspection apparatus according to the second embodiment.

Next, an operational sequence of the inspection apparatus according to the present embodiment is described below using a flowchart of FIG. 9. First, the substrate 101 is mounted on a substrate-holding jig 102 (step 900). A processing unit 106 activates the spindle 103 to rotate the substrate 101 (step 901). After confirming that the rotation of the substrate 101 has reached a fixed rotating speed for inspection, the processing unit 106 moves a moving stage 201 (step 902). The processing unit 106 next detects any ducts arranged near the surface of the substrate 101 (step 903). Of all ducts present on or near the surface of the substrate 101, only those closest to the central section 401 are detected (step 904). A clean hot airflow is supplied from each duct closest to the central section 401 (step 906). Supply of an airflow from ducts other than those which have been determined to be present near the surface of the substrate 101 is stopped (step 905). A clean cold airflow is supplied from the remaining ducts present near the surface of the substrate 101 (step 907). At this time, an airflow is supplied from the ducts facing in the same direction as a tangent direction with respect to the rotation of the substrate 101, and the supply of the airflow from the ducts facing in an opposite direction is stopped.

Figure 8:
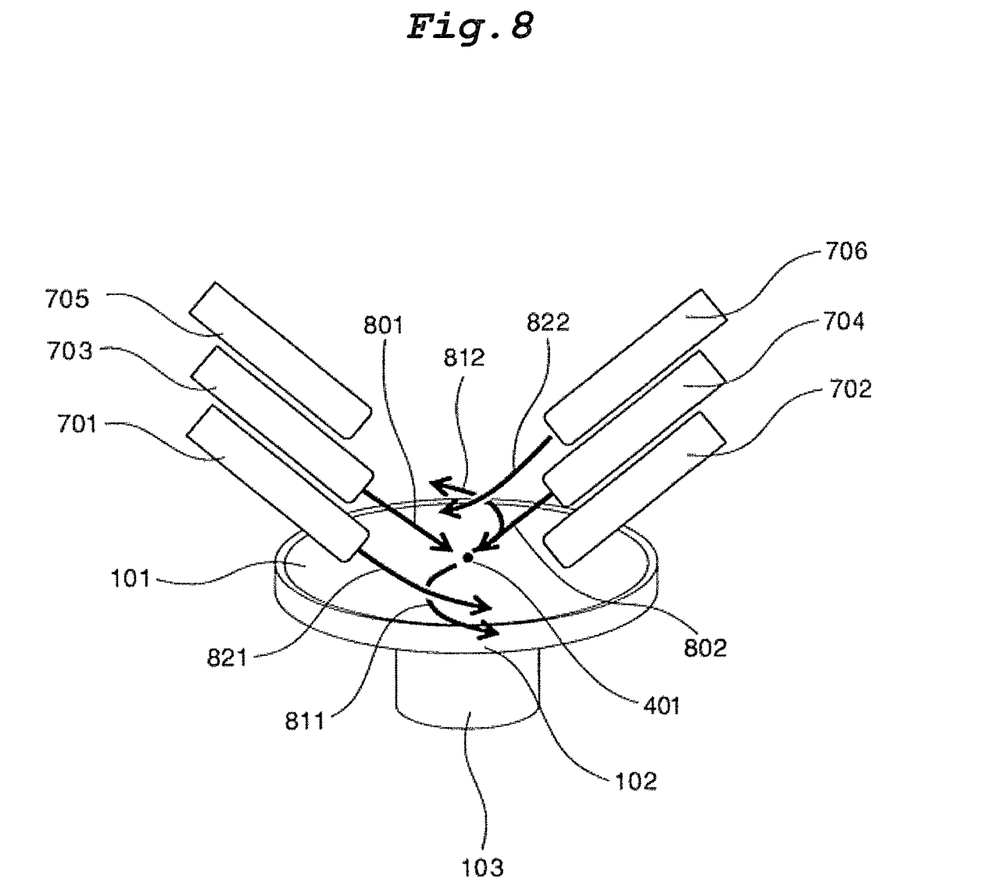
FIG. 8 is a schematic diagram of an airflow supplied from the inspection apparatus according to the second embodiment.

More specifically, as shown in FIG. 8, the present embodiment supplies the clean hot airflows 801, 802 from the ducts 703, 704, and supplies the clean cold airflows 821, 822 only from the ducts 701, 706 whose airflow supply directions match the tangent direction with respect to the rotation of the substrate 101.

In the present embodiment, when the substrate 101 rotates counterclockwise in FIG. 7, airflows are supplied in the following time-series timing with a progress of the movement of the substrate 101:

(1) Supply a clean hot airflow from the ducts 703, 704, and supply a clean cold airflow from the ducts 701, 706
(2) Supply a clean hot airflow from the ducts 705, 706, and supply a clean cold airflow from the ducts 703, 708
(3) Supply a clean hot airflow from the ducts 707, 708, and supply a clean cold airflow from the ducts 705, 710
(4) Supply a clean hot airflow from the ducts 709, 710, and supply a clean cold airflow from the ducts 707, 712

In accordance with the present embodiment, foreign matter can be prevented from sticking. Although an example in which an airflow of a different temperature is supplied above the substrate 101 has been described in the present embodiment, an airflow of much the same temperature, not an airflow of a different temperature, may be used to supply an airflow that streams in the same direction as the tangent direction with respect to the rotation of the substrate 101. Advantageous effects obtained in this case are substantially the same as in the first embodiment.

Third Embodiment

Next, a third embodiment is described below. In the third embodiment, a system configuration that supplies airflows differs from those of the first and second embodiments. While the first and second embodiments have used a plurality of ducts arranged spatially apart from one another, the present embodiment uses substantially one airflow supply system fitted with a plurality of blowout ports.

Figure 10:
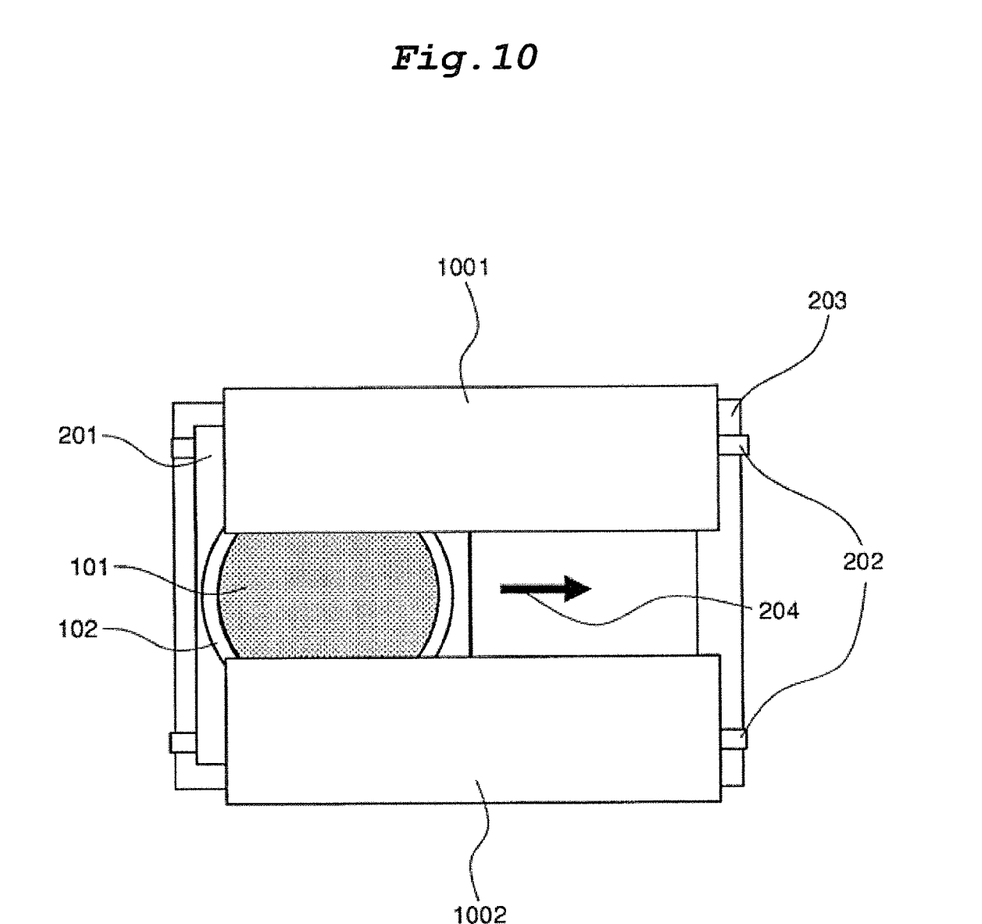
FIG. 10 is a top view showing a schematic configuration of an inspection apparatus according to a third embodiment.

FIG. 10 is a top view illustrating an inspection apparatus existing when viewed from a direction above a substrate 101 in the present embodiment. In the present embodiment, airflow supply systems 1001 and 1002 are arranged in a direction, indicated by arrow 204, where the substrate 101 is carried by a moving stage 201. The airflow supply systems 1001, 1002 supply airflows to a neighborhood of the substrate surface while the moving stage 201 carries the substrate 101.

Figure 11A:
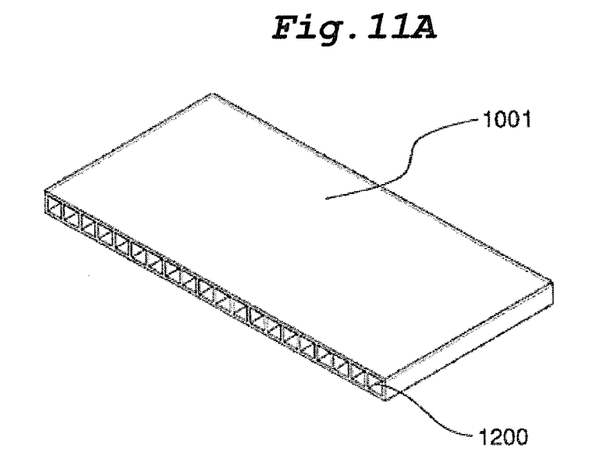
FIGS. 11A, 11B, and 11C are detailed views of an airflow supply system according to the third embodiment.
Figure 11B:
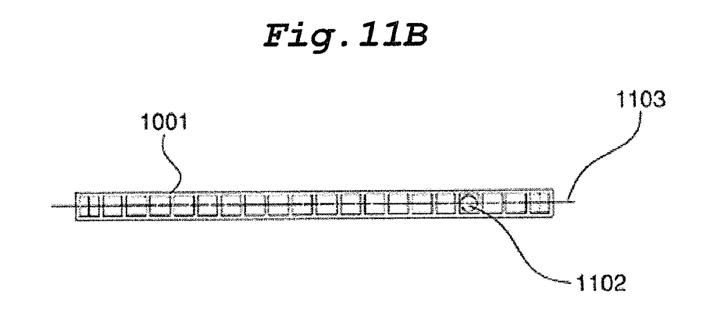
Figure 11C:
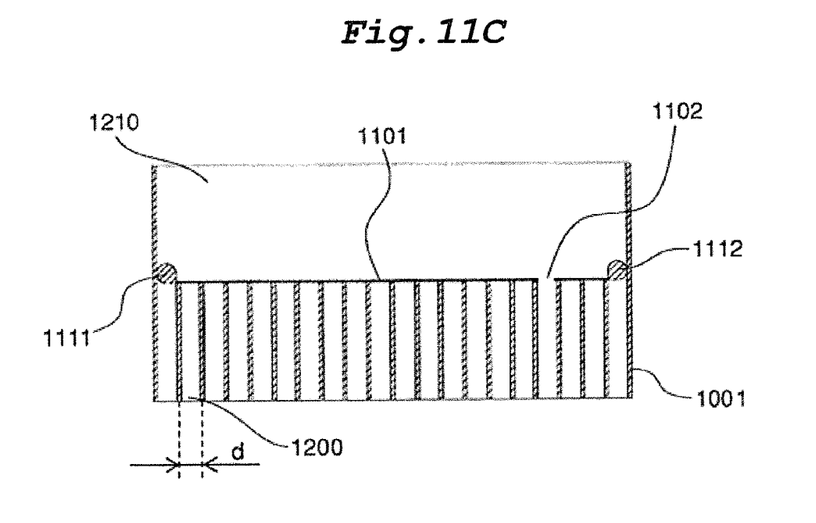

The airflow supply system 1001 is next described in detail below using FIGS. 11A, 11B, and 11C. FIG. 11A is a perspective view of the airflow supply system 1001. FIG. 11B is an external view of the airflow supply system 1001 as viewed from an airflow supply direction, and FIG. 11C is a sectional view of the airflow supply system 1001, at a section 1103 shown in FIG. 11B. The airflow supply system 1002 is of the same structure as that of the system 1001.

The airflow supply system 1001 has a structure with a plurality of ducts adjacent to each other, the ducts each including a blowout port 1200 having a width "d".

As shown in FIG. 11C, each duct forms an independent flow channel around the blowout port 1200. On the inside distant from the blowout port 1200, however, all ducts are coupled to one flow channel 1210.

A belt 1101 with a hole 1102, and two belt take-up mechanisms, 1111 and 1112, are provided inside the airflow supply system 1001. The belt take-up mechanism 1111, 1112 allow a position of the hole 1102 in the belt 1101 to be controlled. In this case, width of the belt 1101 and that of the belt 1102 are set to be nearly equal to the width "d" of the blowout port 1200 of the airflow supply system 1001.

In the airflow supply system 1001, central coordinates of the substrate 101 in FIG. 10 and those of the hole 1102 in the belt 1101 of FIG. 11 can be matched in the direction of arrow 204 shown in FIG. 10, and thus the center of the substrate 101 and a clean airflow supply position can be matched. As a result, even when the substrate 101 is moving horizontally, clean airflows can always be supplied to the center of the substrate 101, for suppressed sticking of foreign matter. To obtain these favorable effects, if the number of ducts with the width "d" is taken as N and the distance through which the moving stage 201 moves is taken as L, then the three parameters are desirably set to satisfy a relationship of d·N>L.

In addition, providing a filter over an entire surface of the blowout port 1200 in the airflow supply system 1001 allows clean airflows to be supplied from the airflow supply system 1001, even if friction occurs between the belt 1101 and the airflow supply system 1001 and/or foreign matter arises from the belt take-up mechanisms 1111, 1112.

Fourth Embodiment

Next, a fourth embodiment is described below. Depending upon a rotating speed of a spindle, the present embodiment changes at least one of a flow rate and flow velocity of a medium supplied to a substrate.

Figure 14:
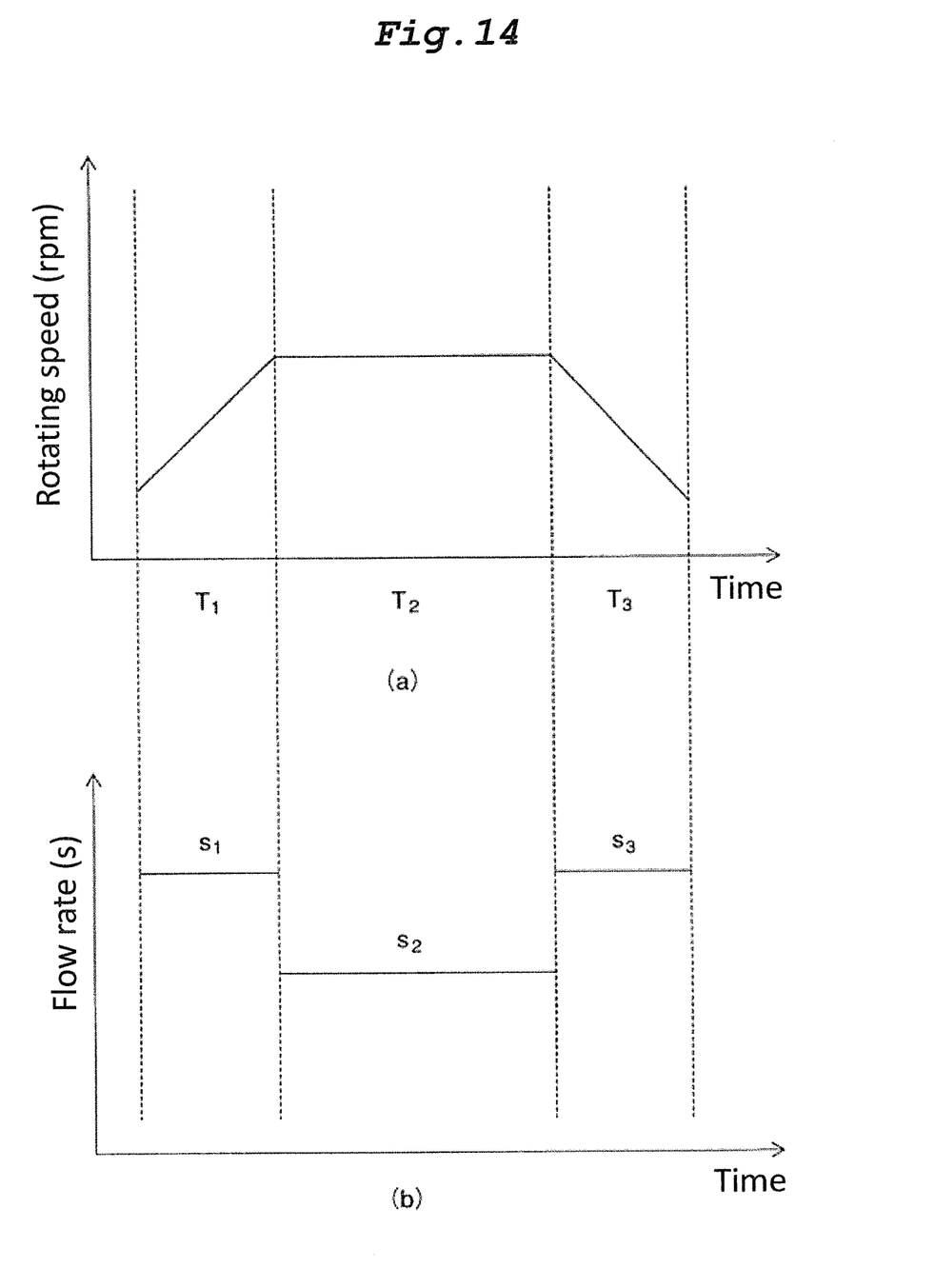
FIGS. 14(a) and 14(b) are explanatory diagrams of a fourth embodiment.

How the flow rate of the medium supplied to the substrate is changed according to the particular spindle speed is first described below. FIGS. 14(*a*) and 14(*b*) are explanatory diagrams of the present embodiment, FIG. 14(*a*) representing a relationship between time and the rotating speed of the spindle 103 in one of the first to third embodiments, and FIG. 14(*b*) representing a relationship between time and the flow rate "v" of an airflow supplied to the substrate 101 in one of the first to third embodiments.

Time $T_1$ denotes a time required for the spindle to reach a desired rotating speed for inspection, time $T_2$ denotes a time during which the inspection is ongoing at the desired spindle speed, and time $T_3$ denotes a time required for the substrate 101 to complete the rotation from an end of the inspection.

During time periods of $T_1$, $T_2$, foreign matter may stick to the substrate 101 more significantly than during any other time periods. In the present embodiment, therefore, a flow rate "$s_1$" within time $T_1$ and a flow rate "$s_3$" within time $T_3$ are set to be higher than a flow rate "$s_2$" within time $T_2$. This helps prevent foreign matter from sticking, even during a non-inspection time.

Figure 15:
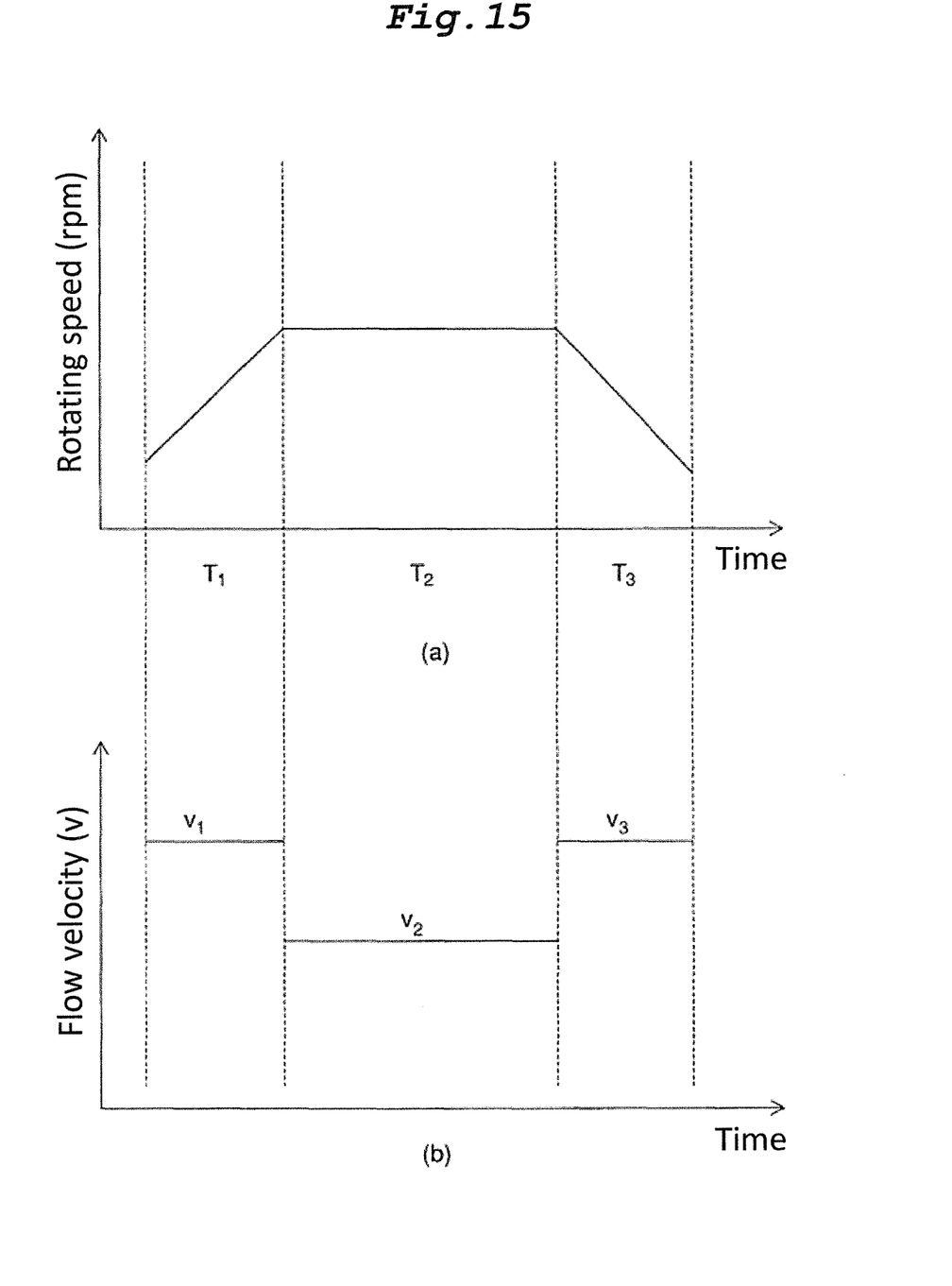
FIGS. 15(a) and 15(b) are additional explanatory diagrams of the fourth embodiment.

How the flow velocity of the medium supplied to the substrate is changed according to the particular spindle speed is next described below. FIGS. 15(*a*) and 15(*b*) are other explanatory diagrams of the fourth embodiment, FIG. 15(*a*) representing a relationship between time and the rotating speed of the spindle 103 in one of the first to third embodiments, and FIG. 15(*b*) representing a relationship between time and the flow velocity "v" of an airflow supplied to the substrate 101 in one of the first to third embodiments.

Time $T_1$ denotes a time required for the spindle to reach a desired rotating speed for inspection, time $T_2$ denotes a time during which the inspection is ongoing at the desired spindle speed, and time $T_3$ denotes a time required for the substrate 101 to complete the rotation from an end of the inspection.

During time periods of $T_1$, $T_2$, foreign matter may stick to the substrate 101 more significantly than during any other time periods. In the present embodiment, therefore, a flow velocity "$v_1$" within time $T_1$ and a flow velocity "$v_3$" within time $T_3$ are set to be higher than a flow velocity "$v_2$" within time $T_2$. This helps prevent foreign matter from sticking, even during a non-inspection time.

While embodiments of the present invention have been described above, contents of the embodiments may also be applied to inspection apparatuses that move the substrate 101 in an X-Y plane direction.

What is claimed is:

1. An apparatus for inspecting a substrate, comprising:
a supply unit that supplies, from two opposing directions, towards an inner circumferential section of the substrate, a medium cleaner than an atmosphere surrounding the substrate;
a rotating unit that rotates the substrate; and
a moving unit that moves the substrate rectilinearly, wherein
the supply unit supplies the medium to the inner circumferential section of the substrate while the moving unit moves.

2. The apparatus according to claim 1, wherein:
the supply unit is formed from two ducts arranged in a facing manner; and
a plurality of the supply units are disposed in a direction that the moving unit moves.

3. The apparatus according to claim 1, wherein:
the supply unit includes a plurality of blowout ports to supply the medium; and
the blowout ports for supplying the medium are selectively switched according to a rate at which the substrate moves.

4. The apparatus according to claim 1, wherein:
the supply unit changes a flow rate of the medium according to a rotating speed at which the substrate rotates.

5. The apparatus according to claim 1, wherein:
the supply unit changes a flow velocity of the medium according to a rotating speed at which the substrate rotates.

6. The apparatus according to claim 1, wherein:
the supply unit changes a temperature of the medium.

7. The apparatus according to claim 1, wherein:
the supply unit supplies a first medium to the inner circumferential section of the substrate and supplies a second medium to an outer circumferential section of the substrate; and
the first medium has a temperature higher than that of the second medium.

8. An apparatus for inspecting a substrate, comprising:
a supply unit that supplies, from two opposing directions, towards an inner circumferential section of the substrate, a medium cleaner than an atmosphere surrounding the substrate; and
a rotating unit that rotates the substrate, wherein
the supply unit changes a flow rate of the medium according to a rotating speed at which the substrate rotates.

9. The apparatus according to claim 8, further comprising:
a moving unit that moves the substrate rectilinearly, wherein
the supply unit supplies the medium to the inner circumferential section of the substrate while the moving unit moves.

10. The apparatus according to claim 8, wherein:
the supply unit is formed from two ducts arranged in a facing manner; and
a plurality of the supply units are disposed in a direction that the moving unit moves.

11. The apparatus according to claim 8, wherein:
the supply unit includes a plurality of blowout ports to supply the medium; and
the blowout ports for supplying the medium are selectively switched according to a rate at which the substrate moves.

12. The apparatus according to claim 8, wherein:
the supply unit changes a flow velocity of the medium according to a rotating speed at which the substrate rotates.

13. The apparatus according to claim 8, wherein:
the supply unit changes a temperature of the medium.

14. The apparatus according to claim 8, wherein:
the supply unit supplies a first medium to the inner circumferential section of the substrate and supplies a second medium to an outer circumferential section of the substrate; and
the first medium has a temperature higher than that of the second medium.

15. An apparatus for inspecting a substrate, comprising:
a supply unit that supplies, from two opposing directions, towards an inner circumferential section of the substrate, a medium cleaner than an atmosphere surrounding the substrate; and
a rotating unit that rotates the substrate, wherein
the supply unit supplies a first medium to the inner circumferential section of the substrate and supplies a second medium to an outer circumferential section of the substrate, and
the first medium has a temperature higher than that of the second medium.

16. The apparatus according to claim 15, further comprising:
a moving unit that moves the substrate rectilinearly, wherein
the supply unit supplies the medium to the inner circumferential section of the substrate while the moving unit moves.

17. The apparatus according to claim 15, wherein:
the supply unit is formed from two ducts arranged in a facing manner; and
a plurality of the supply units are disposed in a direction that the moving unit moves.

18. The apparatus according to claim 15, wherein:
the supply unit includes a plurality of blowout ports to supply the medium, and
the blowout ports for supplying the medium are selectively switched according to a rate at which the substrate moves.

19. The apparatus according to claim 15, wherein:
the supply unit changes a flow rate of the medium according to a rotating speed at which the substrate rotates.

20. The apparatus according to claim 15, wherein:
the supply unit changes a flow velocity of the medium according to a rotating speed at which the substrate rotates.

21. The apparatus according to claim 15, wherein:
the supply unit changes a temperature of the medium.

\* \* \* \* \*